US005857964A

United States Patent [19]
Konstorum et al.

[11] Patent Number: 5,857,964
[45] Date of Patent: Jan. 12, 1999

[54] ENDOSCOPE WITH INTERLOCKING ARTICULATING DEFLECTION SYSTEM

[75] Inventors: Gregory S. Konstorum, Stamford; Edward A. Grabover, Danbury; Ronald M. Callanan, Seymour, all of Conn.; Carlo A. DiRusso, Bronx, N.Y.

[73] Assignee: Circon Corporation, Goleta, Calif.

[21] Appl. No.: 889,513

[22] Filed: Jul. 8, 1997

[51] Int. Cl.[6] ...................................................... A61B 1/00
[52] U.S. Cl. .......................... 600/139; 600/141; 600/142
[58] Field of Search ................................... 600/139, 140, 600/141, 142, 143, 144, 145, 146; 138/118, 120, 155, 166, 167, 168

[56] References Cited

U.S. PATENT DOCUMENTS

| 2,515,366 | 7/1950 | Zublin | 138/120 |
|---|---|---|---|
| 3,583,393 | 6/1971 | Takahashi | 600/142 |
| 4,328,839 | 5/1982 | Lyons et al. | 138/120 |
| 4,651,718 | 3/1987 | Collins et al. | 128/4 |
| 4,762,119 | 8/1988 | Allred, III et al. | 128/4 |
| 5,271,382 | 12/1993 | Chikama | 128/4 |
| 5,448,989 | 9/1995 | Heckele | 600/142 |
| 5,704,898 | 1/1998 | Kokish | 600/142 X |

OTHER PUBLICATIONS

Copy of photographs of links in Fiberscope Model No. 11274AA, Karl Storz Gmbh & Co., 1996.

Primary Examiner—Beverly M. Flanagan
Attorney, Agent, or Firm—Perman & Green, LLP

[57] ABSTRACT

An endoscope having a shaft with a deflectable section. The deflectable section has a plurality of rings movably connected in series to each other. The rings are connected to each other by first and second interlocking sections. The first interlocking sections have eyelet shaped sections. The second interlocking sections have tabs with sections larger than the windows in the eyelet shaped sections.

13 Claims, 3 Drawing Sheets

ENDOSCOPE WITH INTERLOCKING ARTICULATING DEFLECTION SYSTEM

BACKGROUND OF THE INVENTION

1. Field of the Invention

The present invention relates to medical instruments and, more particularly, to an endoscope with a shaft having a deflectable section.

2. Prior Art

U.S. Pat. No. 5,371,382 discloses an endoscope with a shaft having a deflectable section. Tubular segments are pivotably connected to each other by rivets. U.S. Pat. Nos. 4,651,718 and 4,762,119 disclose ball and socket connected links in an endoscope shaft. Karl Storz Gmbh & Co. sells an endoscope called the Fiberscope Model No. 11274AA with a deflectable shaft that has links connected to each other by a T-shaped tab and two entrapping tabs on an adjacent link bent towards each other on opposite sides of the T-shaped tab.

SUMMARY OF THE INVENTION

In accordance with one embodiment of the present invention an endoscope is provided having a shaft with a deflectable section. The deflectable section has a plurality of ring sections connected to each other in series. The ring sections have first ends and opposite second ends with pairs of first and second interlocking sections. Each of the first interlocking sections have a tab and each of the second interlocking sections have a receiving area. The tabs are interlocked with the second interlocking sections in the receiving areas of adjacent ring sections. The improvement comprises the second interlocking sections each having a continuous perimeter around the receiving area to form a window. The tab has a section passed through the window that is larger than the window to prevent disconnection of the adjacent ring sections from each other.

In accordance with another embodiment of the present invention an endoscope is provided having a shaft with a deflectable section. The deflectable section has a plurality of ring sections connected to each other in series. The ring sections have first ends and opposite second ends with pairs of first and second interlocking sections. Each of the first interlocking sections has a tab and each of the second interlocking sections has a receiving area. The tabs are interlocked with the second interlocking section in the receiving areas of the adjacent ring sections. The improvement comprises the tabs each having a portion outwardly formed to make to portions larger than the receiving areas and thereby preventing withdrawal of the tabs through the receiving areas.

In accordance with one method of the present invention a method of manufacturing a shaft for an endoscope is provided comprising steps of providing a plurality of rings with first and second interlocking sections on opposite ends, the first interlocking sections having axially twisted tabs and the second interlocking sections having outwardly bent eyelet sections; inserting the tabs into the eyelet sections; and substantially flattening the tabs and the eyelet sections.

BRIEF DESCRIPTION OF THE DRAWINGS

The forgoing aspects and other features of the invention are explained in the following description, taken in connection with the accompanying drawings, wherein.

DETAILED DESCRIPTION OF THE PREFERRED EMBODIMENTS

Figure 1:
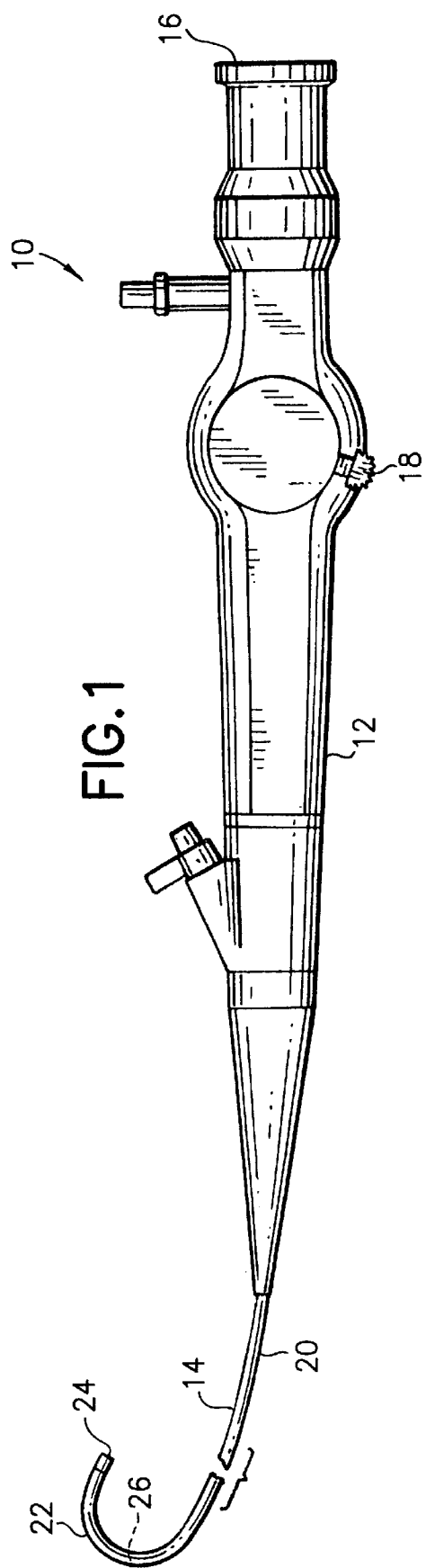
FIG. 1 is an elevational side view of an endoscope incorporating features of the present invention.

Referring to FIG. 1, there is shown an endoscope 10 incorporating features of the present invention. Although the present invention will be described with reference to the embodiments known in the drawings, it should be understood that the present invention can be embodied in various different types and kinds of alternate embodiments. In addition, any suitable size, shape, or type of elements or materials can be used.

The endoscope 10 generally comprises a handle section 12 and a shaft 14. The handle section 12 has an eyepiece 16, and a deflection control lever 18. The handle section is well known in the art and need not be described further. The shaft 14 extends from the front end of the handle section 12. The shaft has a flexible main section 20 and a controllably deflectable section 22 at the distal end of the shaft. Illumination fiber optics, image fiber optics and a working channel (not shown) extend through the shaft 14 from the handle section 12 to the distal tip 24 of the shaft.

Figure 2:
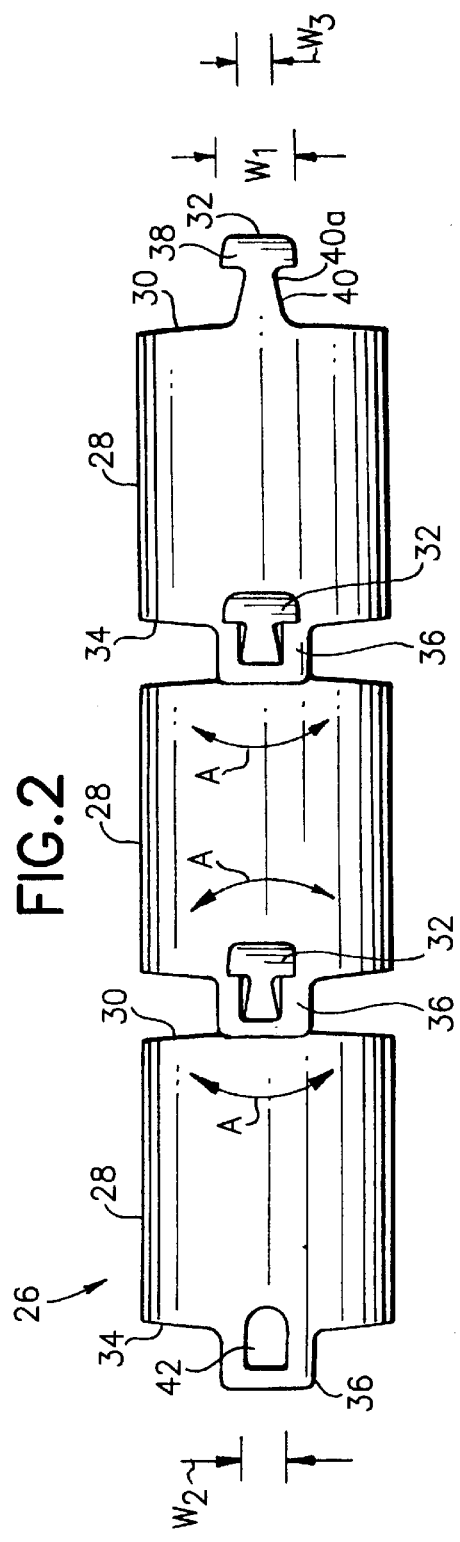
FIG. 2 is an enlarged partial elevational side view of the frame used in the deflectable section of the shaft shown in FIG. 1.
Figure 3:
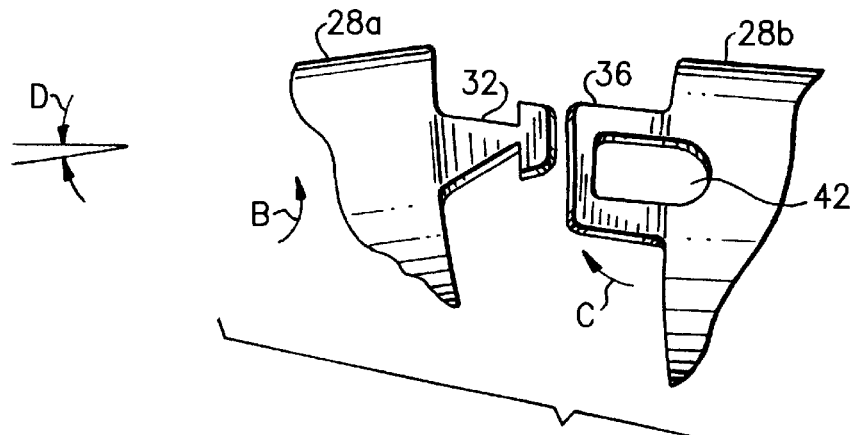
FIGS. 3–6 show various steps used in forming the frame shown in FIG. 2.

The controllably delectable section 22 of the shaft 14 has a frame 26. Referring also to FIG. 2, a portion of the frame 26 is shown. The frame 26 is comprised of links 28 connected to each other in series. The links 28 are preferably comprised of metal, such as stainless steel, and have a general ring or tube shape. Located at a first end 30 of each link 28 are two tabs 32 which are 180° apart; one on each side (only one of which is shown because only one side is shown in FIG. 2). Located at a second end 34 of each link 28 are two eyelet sections 36 which are 180° apart; one on each side (only one of which is shown because only one side is shown in FIG. 2). The tabs 32 are part of a first interlocking section of the links. The eyelet sections 36 are part of a second interlocking section of the links. The eyelet sections 36 have a through opening 42 that forms a receiving area and, more particularly, a continuous perimeter around the receiving area 42 forms a window.

The tabs 32 pass through the windows 42 of the adjacent links 28. The heads 38 of the tabs 32 have a width $W_1$ which is larger than the width $W_2$ of the window 42. This prevents the two interlocking sections from being pulled apart. The narrowest part 40a of the neck 40 has a width $W_3$ adjacent the head 38 that is smaller than the width $W_2$. This type of connection allows the adjacent links 28 to be articulatable relative to each other as indicated by arrows A. The degree of maximum articulation between adjacent links is only about 15°. However, because there are a plurality of the links 28 connected in series, the controllable deflectable section 22 can be articutable 180° or more in two opposite directions.

Figure 4:
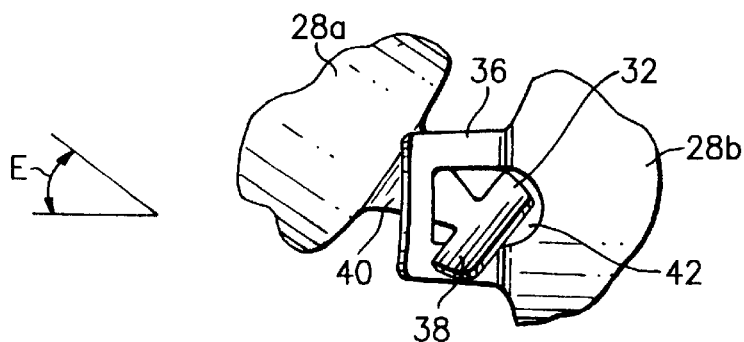
Figure 5:
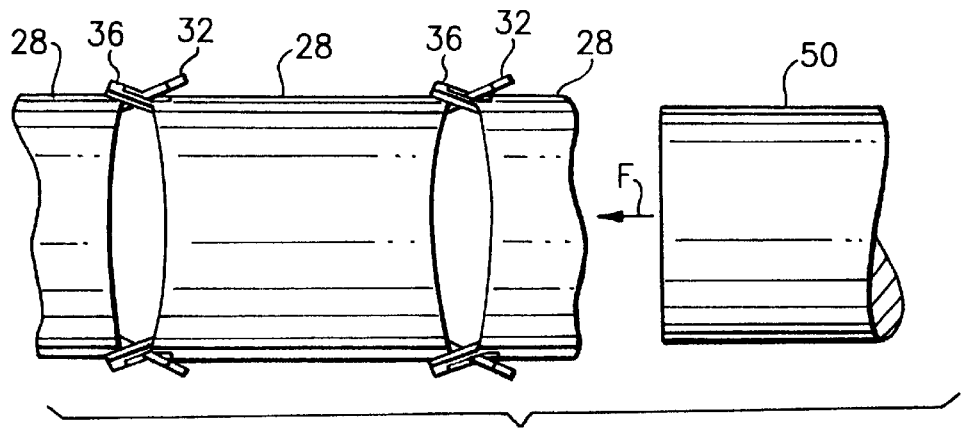
Figure 6:
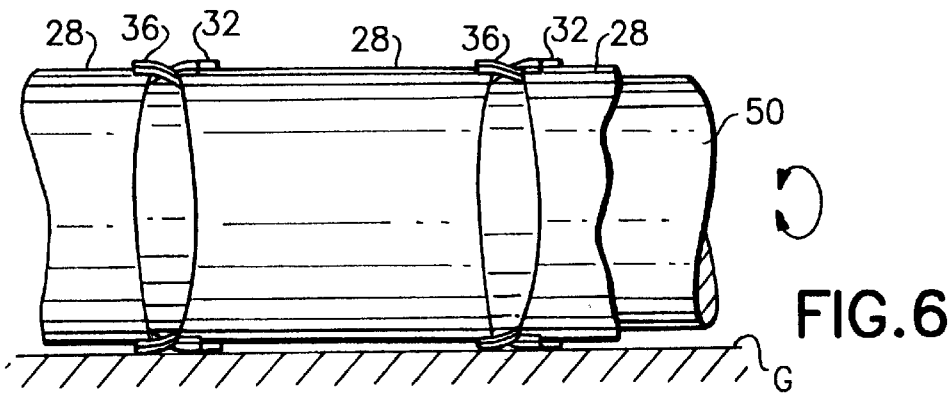

Referring also to FIGS. 3–6, the method of attaching the links to each other will be described. The individual links 28 are initially provided with their tabs 32 axially twisted as seen best in FIG. 3. The degree of axial twist B is preferably about 45°. The eyelet sections 36 are outwardly bent at angle C at about 20°. However, other angles could be used. As seen in FIG. 4, the head 38 of the tab 32 is inserted through the window 42. Thus, the neck 40 extends through the window 42. Preferably, a first tab 32 is inserted into its respective window and then a second tab 32 on the same end is inserted through its respective window. When the second tab is inserted into its respective window, it snaps through the window to thereby interlock the two links. As seen in comparing FIGS. 3 and 4, the first link 28a is moved from a relative angle D with the second link 28b to a relative angle E in order to pass the head 38 through the window 42. As seen in FIG. 5, after assembly of the links 28, tabs 32 and eyelet sections 36 extend outward from the frame 26. A back support rod 50 is inserted into the links 28 as shown by arrow F. The rod 50 has an outer diameter substantially the same as the inner diameter of the links 28. As seen in FIG. 6, the frame 26 is then rolled on a flat surface G. This flattens the tabs 32 and eyelet sections 36 against the side of the frame 26. The back support rod 50 is then removed. The rod 50 prevents the links 28 from being crushed during the flattening process.

The interconnection described above provides two principle advantages over the prior art tabs used in the Fiberscope Model No. 11274AA described above. First, the present invention has greater resistance to pull out of the interlocking sections. In the prior art, the entrapping tab arms could deflect outward to allow separation to occur. However, with the present invention separation can only occur if there is a catastrophic failure; i.e.: the tab 32 or eyelet section 36 has to rip apart. Thus, the amount of force necessary to separate two links is increased. Second, the present invention provided increased resistance to torque deformation. Because the eyelet section 36 is a unitary closed loop, it has a greater structural integrity than two cantilevered beams as in the prior art entrapping tabs. This structural loop adds strength to increase resistance to torque deformation. These two increases in resistance can provide a deflectable section frame with an increased working life.

Figure 7:
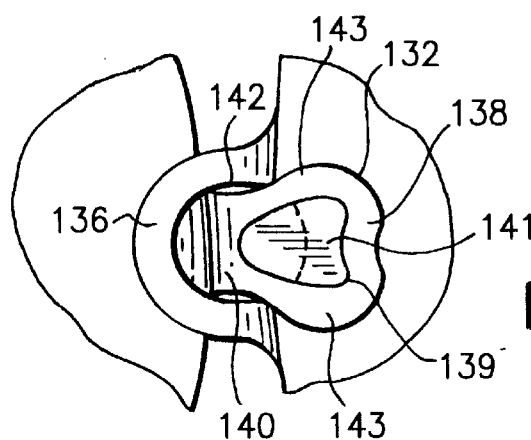
FIG. 7 shows a connection between two links of an alternate embodiment of the present invention.

Referring to FIG. 7 an alternate embodiment is shown. In this embodiment the eyelet sections 136 have a curved arch shape with a circular window 142. The tabs 132 have a neck 140 and a head 138. The head 138 has a loop shape with a center aperture 139. The two side arms 143 of the loop shaped head 138 are closer to each other than shown in FIG. 7 before the head 138 is inserted through the window 142. After the head 138 is passed through the window 142 a tool is then used to spread the side arms 143 apart and thereby make the head 138 larger then the window 142. This prevents withdrawal of the head 138 through the window 142 and thereby interlocks the two links to each other. In the embodiment shown, a filler 141 is inserted into the center aperture 139 to act as a stiffener and to prevent the arms 143 from collapsing towards each other. However, the filler need not be used.

Figure 8A:
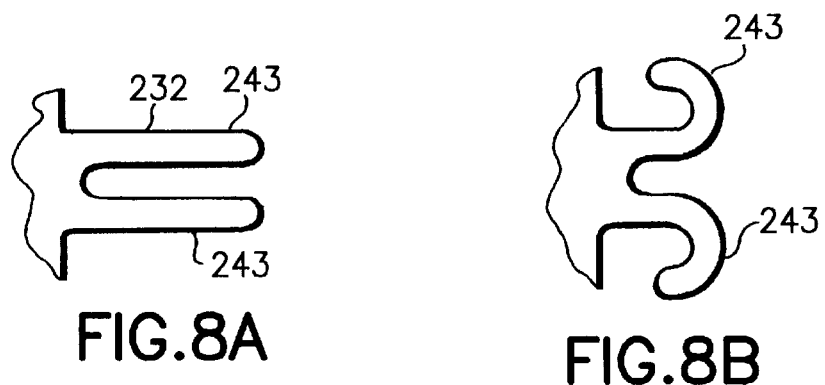
FIG. 8A and 8B show another alternate embodiment of the present invention.
Figure 8B:
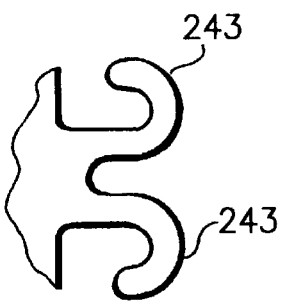

FIGS. 8A and 8B show another alternate embodiment of the tab 232. In this embodiment each tab 232 has two arms 243. The arms 243 are deformed from their straight shape shown in FIG. 8A to their opposite hooked shapes shown in FIG. 8B after the arms 243 are inserted into an eyelet section. This hooks the tab 232 to the eyelet section, but still allows pivotable motion between the two links.

Figure 9:
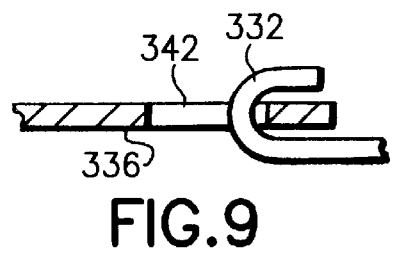
FIG. 9 shows another alternate environment of a connection incorporating features of the present invention.

FIG. 9 shows another alternate embodiment of the invention. In this embodiment the tab 332 is bent outward and around through a window 342 of the eyelet section 336 and brazened to itself. The tab 332 could be brazened to the eyelet section 336 if articulated motion is not desired.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. In an endoscope having a shaft with a deflectable section, the deflectable section having a plurality of ring sections connected to each other in series, the ring sections having first ends and opposite second ends with pairs of first and second interlocking sections, each of the first interlocking sections having a tab and each of the second interlocking sections having a receiving area, the tabs being interlocked with the second interlocking sections in the receiving areas of adjacent ring sections, wherein the improvement comprises:

the second interlocking sections each having a continuous perimeter around the receiving area to form a window, wherein the tab has a section passed through the window that is larger than the window to prevent disconnection of the adjacent ring sections from each other.

2. An endoscope as in claim 1 wherein the tabs have a general "T" shape.

3. An endoscope as in claim 1 wherein the tabs have a general expanded loop shape.

4. An endoscope as in claim 1 wherein the tabs have prongs that are outwardly deformed to hook onto the second interlocking sections.

5. In an endoscope having a shaft with a deflectable section, the deflectable section having a plurality of ring sections connected to each other in series, the ring sections having first ends and opposite second ends with pairs of first and second interlocking sections, each of the first interlocking sections having a tab and each of the second interlocking sections having a receiving area, the tabs being interlocked with the second interlocking sections in the receiving areas of adjacent ring sections, wherein the improvement comprises:

the tabs each having a portion that is outwardly deformed to make the portions larger than the receiving areas and thereby prevent withdrawal of the tabs from the receiving areas, wherein the second interlocking sections have an eyelet shape with a window surrounded by a continuous perimeter.

6. An endoscope as in claim 5 wherein the tabs have a general expanded loop shape.

7. An endoscope as in claim 6 wherein an aperture in the expanded loop shape is filled with a filler.

8. An endoscope as in claim 5 wherein the tabs have prongs that are outwardly deformed to hook onto the second interlocking sections.

9. A method of manufacturing a shaft for an endoscope, the method comprising steps of:

providing a plurality of rings with first and second interlocking sections on opposite ends, the first interlocking sections having an axially twisted tabs and the second interlocking sections having outwardly bent eyelet sections;

inserting the tabs into the eyelet sections; and substantially flattening the tabs and the eyelet sections.

10. A method as in claim 9 wherein the step of providing comprises axially twisting the tabs about 45°.

11. A method as in claim 9 wherein the step of providing comprises outwardly bending eyelet sections about 20°.

12. A method as in claim 9 wherein the step of inserting comprises inserting a first tab into a first eyelet section and then inserting a second tab into a second eyelet section, wherein the second tab snap locks into the second eyelet section.

13. A method as in claim 9 wherein the steps of substantially flattening comprises inserting a rod into the rings as a back support and rolling the rings on a flat surface.

* * * * *